United States Patent [19]

Koropp

[11] Patent Number: 4,868,845
[45] Date of Patent: Sep. 19, 1989

[54] X-RAY APPARATUS WITH A MOVABLE PART

[75] Inventor: Norbert Koropp, Reinbek, Fed. Rep. of Germany

[73] Assignee: U.S. Philips Corporation, New York, N.Y.

[21] Appl. No.: 43,017

[22] Filed: Apr. 27, 1987

[30] Foreign Application Priority Data

Apr. 26, 1986 [DE] Fed. Rep. of Germany ....... 3614295

[51] Int. Cl.$^4$ .............................................. G05B 11/01
[52] U.S. Cl. ................................... 378/204; 378/208; 378/183; 378/197; 248/333
[58] Field of Search ............... 378/193, 195, 196, 197, 378/198, 204, 205, 208, 209; 248/323, 327, 333, 325, 188.4

[56] References Cited

U.S. PATENT DOCUMENTS 3,556,455  1/1971  Storm .................................. 248/333
4,677,273  6/1987  Colegrove et al. ................. 248/333

FOREIGN PATENT DOCUMENTS 2104509  8/1972  Fed. Rep. of Germany .
2361985  6/1975  Fed. Rep. of Germany .

Primary Examiner—Craig E. Church
Assistant Examiner—Joseph A. Hynds
Attorney, Agent, or Firm—Thomas A. Briody; Jack E. Haken; Jack D. Slobod

[57] ABSTRACT

The invention relates to an X-ray apparatus with a motor-driven movable part. The drive takes place via a shaft, which is mounted in a bearing, the bearing forces of which are measured by a measuring device.

8 Claims, 3 Drawing Sheets

X-RAY APPARATUS WITH A MOVABLE PART

BACKGROUND OF THE INVENTION

The invention relates to an X-ray apparatus with a movable part, having a measuring device which measures the forces exerted on the accessory and appropriately controls the drive therefore. Such an X-ray apparatus is known (German Offenlegungsschrift Nos. 2,104,509 and 2,361,985).

In order to prevent a situation in which the patient is squeezed by the accessory moved by the force of the drive motor or the accessory travels to the floor or the ceiling of the examination room, it is necessary to provide a measuring device, which measures the force exerted on the accessory and deactuates the drive if the forces exerted on the accessory vary to a predetermined extent. In the known devices, the motor drive is connected to the accessory via a cable, and the measuring device detects the forces acting on the cable. This demands that, in the event of an exchange of the cable, the measuring device—in general, a wire strain gauge—must also be exchanged since it must be adapted to the properties of the cable.

SUMMARY OF THE INVENTION

The object of the present invention is to develop an X-ray apparatus of the initially mentioned type in such a manner that the drive can take place without a cable. This object is achieved, according to the invention, in that the drive takes place via a shaft, which is provided with at least one bearing, and in that the measuring device measures the forces exerted on the bearing in the direction of the shaft. The drive shaft transmits the forces acting on the accessory to the bearing where they can be measured in a simple and reliable manner.

A refinement of the invention provides that the bearing is connected to a fixed part of the X-ray device via a deformable body and that the deformable body is provided with sensors which measure its deformation, a wire strain gauge preferably being provided as sensor. The (elastically) deformable body, which preferably surrounds the shaft in the manner of a barrel, can be produced in a simple manner and forms, together with one or more wire strain gauges fitted to it, a robust and reliable component.

A further development of the invention provides that the shaft is provided with a spur wheel, which is coupled with the drive and which cooperates with a spur wheel coupled to the accessory. This further development utilizes the fact that forces act on the helical spur gears, in the direction of the shaft on which the gears are fitted, proportional to the force exerted by the motor drive or the accessory on the shaft. By measurement of this force, it is possible to determine the turning moment, and, if a limiting value is exceeded, the motor drive can be deactuated.

BRIEF DESCRIPTION OF THE DRAWING

The invention is explained in greater detail below, with reference to the drawing. In the drawing.

DESCRIPTION OF THE PREFERRED EMBODIMENTS

Figure 1:
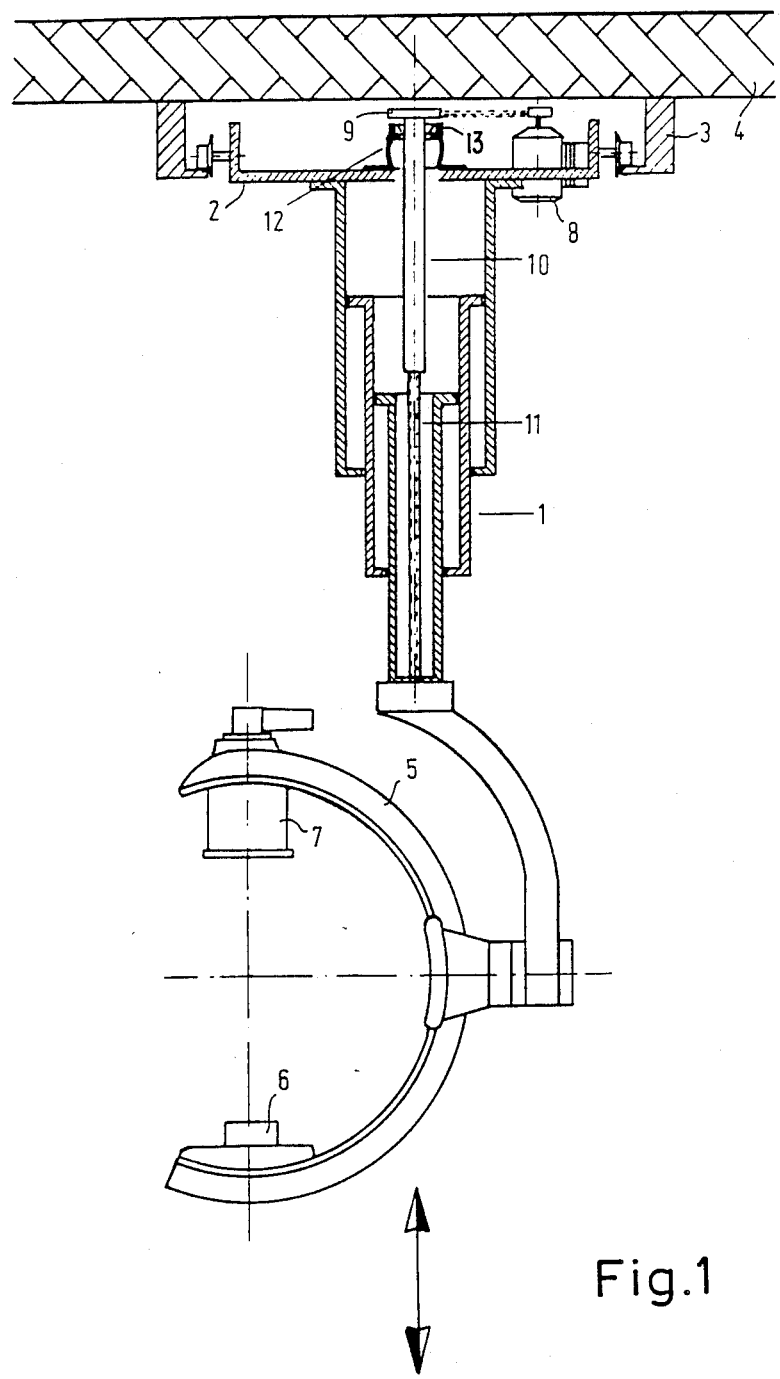
FIG. 1 shows an X-ray device according to the invention, which device is secured as a C arc device at a ceiling support.

In FIG. 1, 1 designates a ceiling support, which comprises a plurality of hollow cylindrical parts which are displaceable within one another telescopically. Ceiling support 1 is secured at a support carriage 2 which is movable in rails 3 at the ceiling 4 of an examination room. The ceiling support 1 carries at a tube arc 5 an X-ray source 6 and an image intensifier 7, which are aligned relative to one another.

The outward and inward movement of the ceiling support takes place by means of a motor 8, which acts on a pinion 9 which is secured at a vertical hollow shaft 10. The hollow shaft 10 is provided with an internal thread, into which a threaded spindle 11 engages. Spindle 11 is fixedly connected to the lowermost part of the ceiling support. Depending upon the direction of rotation of the motor 8, the ceiling support is moved either upwards or downwards thereby.

The hollow shaft 10 is mounted in a bearing 13, which is connected to the carriage 2 via a barrel-shaped elastic bearing support 12. The elastic bearing support 12 is provided with one or more wire strain gauges, which measure the deformation of the bearing and place the drive motor 8 at standstill if the deformation or the forces excerted by the load 5 . . . 7 on the bearing exceed a predeterminable value.

It is also possible to interchange the threaded spindle 11 and the hollow shaft 10 with one another, so that the hollow shaft is connected to the lower part of the ceiling support and the threaded spindle to the drive pinion.

Figure 2:
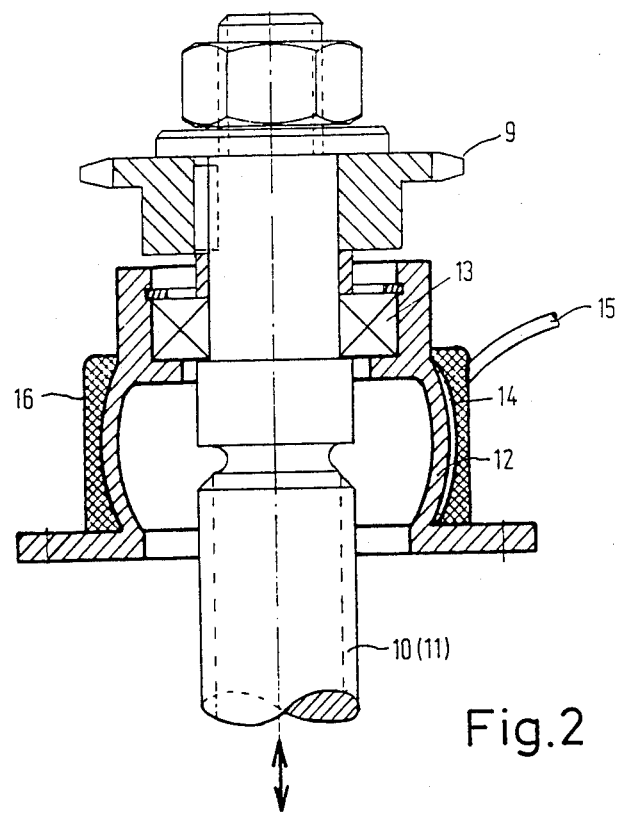
FIG. 2 shows a part of such an X-ray device.

FIG. 2 shows how the hollow shaft 10 or the threaded spindle 11 is secured at the carriage 2. As is evident therefrom, the shaft 10 or 11 is borne by a bearing 13, which is connected, via the elastic bearing support 12, surrounding the shaft 10 (11) in the manner of a barrel, to the carriage 2, which is not shown in greater detail in FIG. 2. To the elastic bearing support 12 there is fitted at least one wire strain gauge, by means of which the deformation of the bearing support 12 is converted into an electrical signal and which is provided via a connecting line 15 with a control circuit for the drive motor. A protective sleeve 16 consisting of a elastomer is drawn over the strain gauge or strain gauges.

Figure 3:
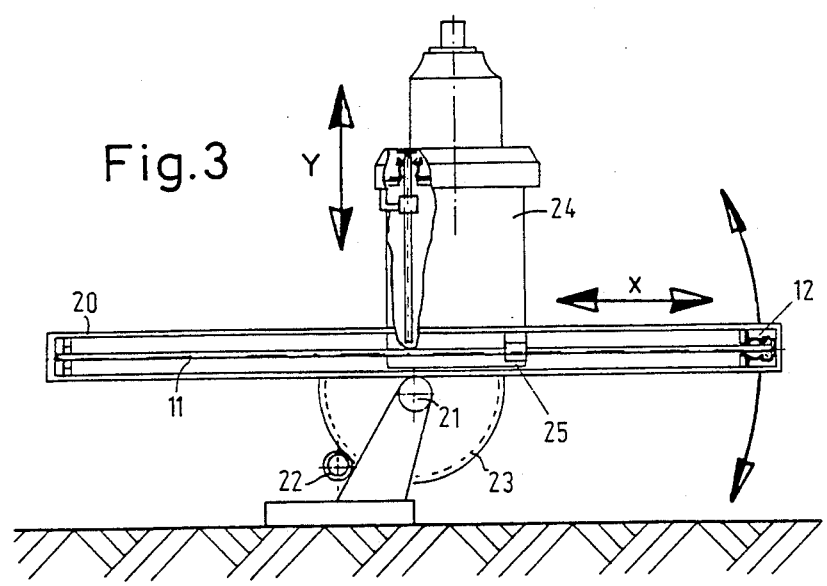
FIG. 3 shows an X-ray device which is movable about a horizontal axis and FIG. 4 shows a part of a tilt drive suitable in the case of a device according to FIG. 3.

FIG. 3 shows an X-ray examination device with a patient support table 20, which can be tilted about a horizontal axis 21 by means of a drive motor 22, which acts on a tooth segment 23 connected to the table plate 20. An X-ray targeting device 24 is movable, by means of the threaded spindle 11 which engages in a spindle nut 25 secured at the targeting device 24, in the longitudinal direction of the table by means of an electric motor which is not shown in greater detail. The threaded spindle is secured, at least at one side, at a bearing, which is connected via an elastic bearing support, as shown in FIG. 2, to the frame of the patient support table 20. The displacement of the targeting device in the compression direction, i.e. perpendicular to the table plate, can take place—as is evident from FIG. 3—by means of an analogously designed drive.

The forces measured by the bearing support are critically dependent upon the position of the table plate 20. They are minimal in the horizontal table plate position shown in the drawing and maximal in the vertical position of the table plate; between these positions, they vary with the sine of the pivot angle. In order, in this case also, to be able to encompass, in addition, the patient support table, the signal supplied by the wire strain gauge connected to the bearing support must be compared with a signal which varies sinusoidally with the pivot angle and which is obtained, for example, from a sine potentiometer, which is coupled to the drive 22.

In devices of the type shown in FIG. 3, it is not only important to supervise the displacement movements of the X-ray targeting device in the longitudinal direction of the table and perpendicular thereto, but also to supervise the tilting movement of the patient support plate, in order to avoid the situation in which the table plate strikes the floor or an obstruction situated thereon during tilting.

Figure 4:
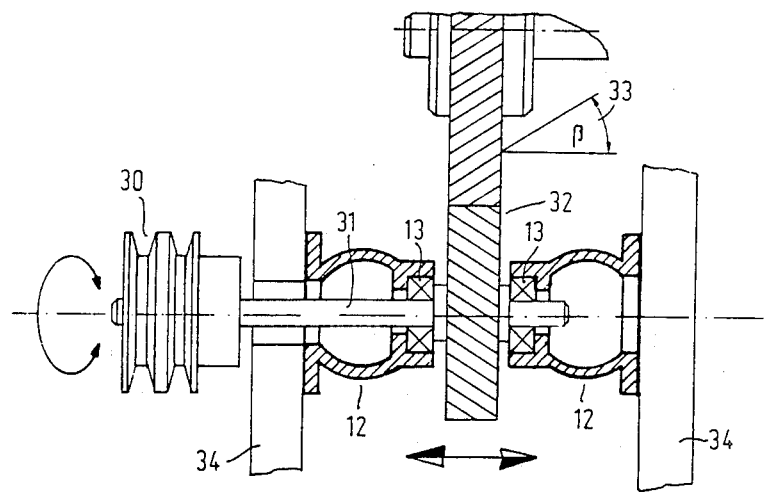

FIG. 4 shows a part of a drive suitable for this. The motor force is transmitted by means of a belt pulley 30 to a shaft 31, on which a helical spur gear 32 is situated, the flanks of which extend at an angle $\beta$ to the direction of the shaft. The helical spur gear 32 cooperates with a further helical spur gear 33, which is coupled to the tooth segment 23 (FIG. 3) in a manner not shown in greater detail. The helical spur gear 32 is borne on both sides in bearings 13, which are connected via the elastic bearing supports 12 in each instance to a part 34 which is fixed in the axial direction of the shaft 31. When the drive is operative, there acts on the helical spur gears 32 a thrust force in the direction of the shaft 31, the magnitude of which is dependent upon the turning moment and the direction of which is dependent upon the direction of rotation. It can be detected by the sensors—preferably wire strain gauges—secured at the bearing supports 12.

Figure 5:
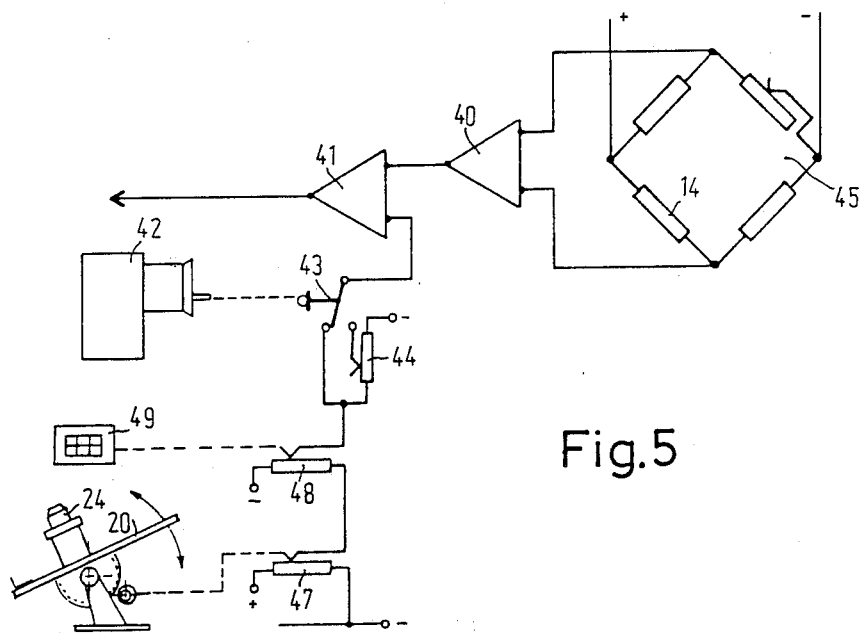

FIG. 5 shows a control circuit for influencing the drive motor. The forces acting on the accessory cause a deformation of the elastic bearing support and thereby a variation of the resistance of the wire strain gauge. This variation of resistance is converted, in a resistance measuring bridge 45, into an electrical voltage, which is amplified by an amplifier 40 and is fed to one of the inputs of a comparator 41. In the case of a device as shown in FIG. 1, the voltage at the other input can be constant. However, in the event that an additional device, e.g. a 100 mm film camera 42 should be connected at the device 5 to 7, the weight which is varied thereby must be taken into account by a variation of the comparative voltage. This can take place, for example, in that be means of a switch contact coupled to the additional device, a change-over switch 43 is changed over, which in a first switch position connects the comparative input of the comparator 41 to the direct voltage at a potentiometer 44 and in the other switch position connects the same to the direct voltage at a tap of this potentiometer.

The loading which is variable in the case of a device according to FIG. 3 as a function of the pivot position of the device can be taken into account by means of a further potentiometer 47, the tap of which is coupled to the tilt drive. The weight of the patient, which is of significance in the tilting of the patient support plate, can be taken into account, for example, in that the voltage at the comparative input of the comparator 41 is tapped off from the tap of a potentiometer 48, which is adjustable—e.g. by a keyboard 49—in dependence upon the weight of the patient.

The three potentiometers 44, 47 and 48 can, if appropriate, also be connected in cascade.

What is claimed is:

1. X-ray apparatus with a movable part, having a measuring device which measures forces exerted on the movable part and appropriately controls the drive therefore, characterized in that the drive takes place via a shaft which is provided with at least one bearing, said bearing being connected to a fixed part of the x-ray apparatus via a deformable body, said deformable body is provided with sensors which measure its deformation and therein measure forces exerted in both directions of the shaft.

2. X-ray apparatus according to claim 1, characterized in that the deformable body is provided with wire strain gauges.

3. X-ray apparatus according to one of the preceding claims, characterized in that the shaft is provided with a spur wheel, which is coupled to the drive and which cooperates with a spur wheel coupled to the movable part.

4. An X-ray apparatus comprising:
   a stationary part including a deformable body mounted thereon;
   a bearing mounted on said deformable body;
   a shaft having a longitudinal axis extending in two opposite directions, said shaft being rotatably mounted on the stationary part by way of the bearing;
   a moveable part coupled to the shaft, said movable part being moveable with respect to the stationary part;
   drive means for rotating the shaft about its axis to move the moveable part; and
   means for measuring forces exerted on the bearing in both directions along the longitudinal axis, the force measuring means comprise means for measuring the deformation of said deformable body, said force-measuring means controlling the drive means in response to said measured forces.

5. An X-ray apparatus as claimed in claim 4, characterized in that the deformable body comprises at least one wire strain gauge.

6. An X-ray apparatus as claimed in claim 5, characterized in that the moveable part is coupled to the shaft by way of two spur wheels.

7. An X-ray apparatus comprising:
   a stationary part including a deformable body mounted thereon;
   a bearing mounted on said deformable body;
   a shaft having a longitudinal axis extending in two opposite directions, said shaft being rotatably mounted on the stationary part by way of the bearing;
   a moveable part coupled to the shaft, said movable part being moveable with respect to the stationary part;
   drive means for rotating the shaft about its axis to move the moveable part; and
   means for measuring forces exerted on the bearing in both directions along the longitudinal axis, the force measuring means comprise means for means for measuring the deformation of said deformable body, said force-measuring means controlling the drive means in response to said measured forces, said force-measuring means further comprising at least one wire strain gauge supporting the bearing.

8. An X-ray apparatus as claimed in claim 7, characterized in that the force-measuring means comprises at least one strain gauge embedded in a protective flexible sleeve.

* * * * *